United States Patent [19]

Levy

[11] Patent Number: 5,540,695
[45] Date of Patent: Jul. 30, 1996

[54] OSTEOTOMY CUTTING GUIDE

[75] Inventor: Michael S. Levy, Wood-Ridge, N.J.

[73] Assignee: Howmedica Inc., New York, N.Y.

[21] Appl. No.: 198,735

[22] Filed: Feb. 18, 1994

[51] Int. Cl.$^6$ .......................... A61B 17/15; A61B 17/17
[52] U.S. Cl. .................................. 606/87; 606/96
[58] Field of Search ........................... 606/86, 87, 88, 606/89, 96, 97, 98

[56] References Cited

U.S. PATENT DOCUMENTS

| | | | |
|---|---|---|---|
| 4,335,715 | 6/1982 | Kirkley | 128/92 EB |
| 4,349,018 | 9/1982 | Chambers | 128/92 E |
| 4,421,112 | 12/1983 | Mains et al. | 606/75 |
| 4,565,191 | 1/1986 | Slocum | 128/92 H |
| 4,750,481 | 6/1988 | Reese | 128/92 VY |
| 4,852,558 | 8/1989 | Outerbridge | 128/92 YF |
| 4,901,711 | 2/1990 | Goble et al. | 606/97 |
| 4,944,739 | 7/1990 | Torre | 606/53 |
| 4,952,213 | 8/1990 | Bowman et al. | 606/88 |
| 4,952,214 | 8/1990 | Comparetto | 606/87 |
| 5,021,056 | 6/1991 | Hofmann et al. | 606/86 |
| 5,049,149 | 9/1991 | Schmidt | 606/88 |
| 5,053,039 | 10/1991 | Hofmann et al. | 606/87 |
| 5,246,444 | 9/1993 | Schreiber | 606/87 |

OTHER PUBLICATIONS

Mynerts, Rune. "The SAAB Jig: An Aid in High Tibial Ostostomy" *ACTA Orthopaedic Scandanavia*, 1978, vol. 49 pp. 85–88.
Lippert and Kirkpatrick, "A Jig for Pin Insertion in the Performance of High Tibial Osteotomy." *Clinical Orthopaedics and Related Research*, V. 112, Oct. 1975, pp. 242–244.

Primary Examiner—Michael H. Thaler
Assistant Examiner—Scott B. Markow
Attorney, Agent, or Firm—Peter C. Richardson; Lawrence C. Akers; Elizabeth O. Slade

[57] ABSTRACT

An osteotomy cutting guide is disclosed. The cutting guide utilities an angle cutting block which is removably and adjustably attached to a stabilizing base. Also utilized is a distal hole drill block which is removably and adjustably attached to the stabilizing base. The stabilizing base has at least one projecting element which can be inserted into an existing cut. The osteotomy cutting guide allows angled cuts and implant insertions to be performed with accuracy.

11 Claims, 11 Drawing Sheets

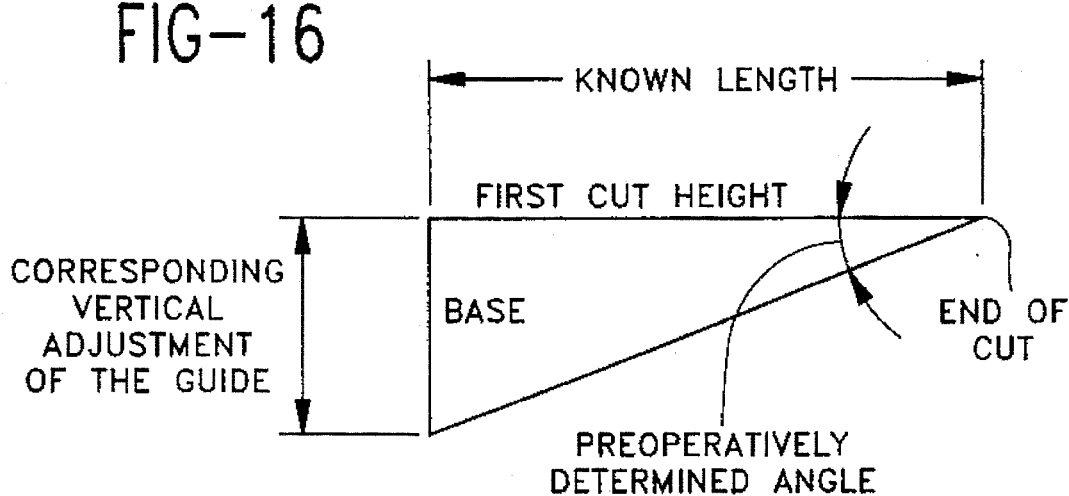
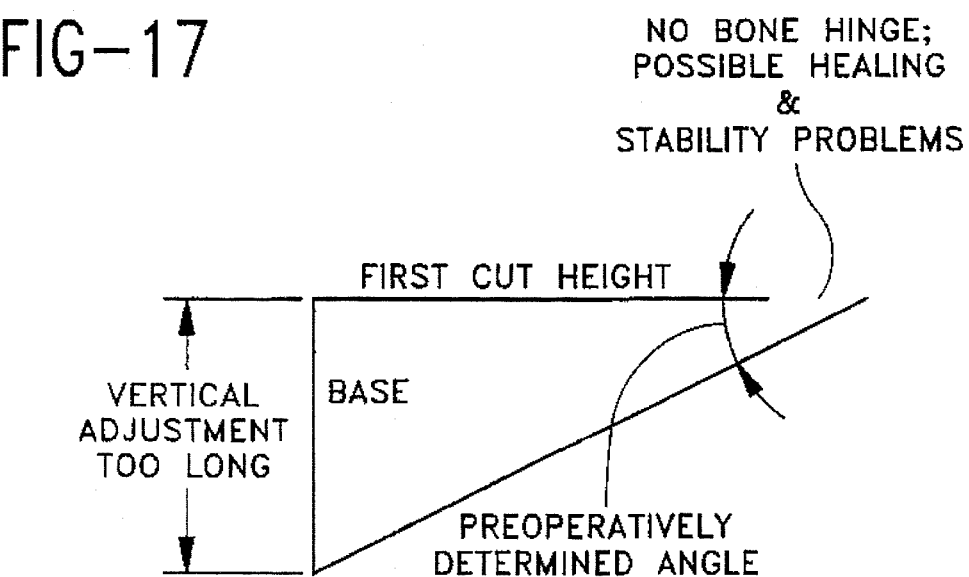
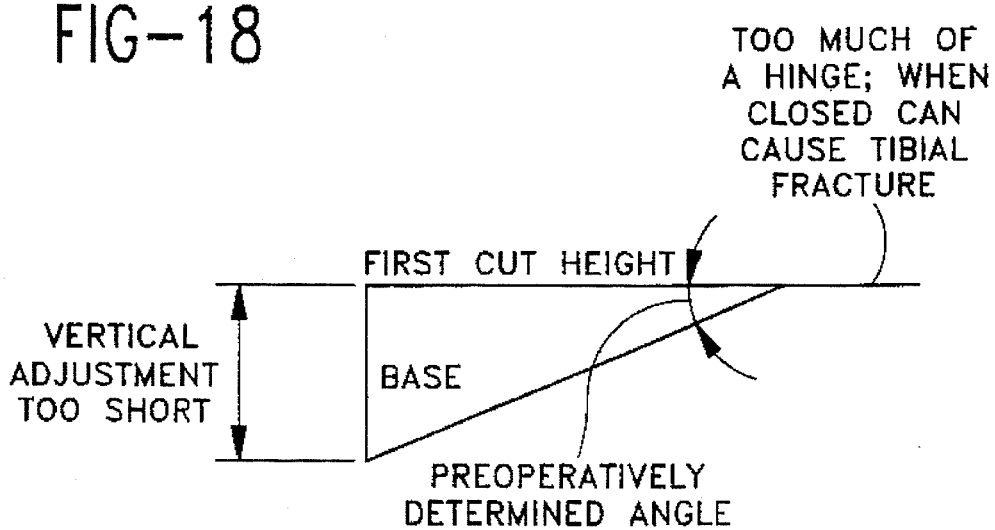

OSTEOTOMY CUTTING GUIDE

BACKGROUND OF THE INVENTION

This invention relates to an apparatus and method for performing an osteotomy. More particularly, it relates to an apparatus and method which allows angled cuts and implant insertions to be performed with accuracy.

Certain bone related problems can be corrected by removing a wedge of bone and realigning the remaining bone segments. This technique is generally known as osteotomy. Several techniques exist for performing osteotomy, but in each case it is generally necessary to perform the cuts accurately to ensure correct realignment of the bone. The cuts should be planar so that severed bone faces mate uniformly to promote rapid and structurally effective mending of the bone.

High tibial osteotomy has become an established means of treating unicompartmental degenerative arthritis of the knee. This technique aligns the lower extremity such that the axis of weight bearing is shared between the medial joint compartment and the lateral joint compartment. Thus, in cases where arthritis predominantly affects the medial joint compartment, a high tibial osteotomy directs the forces of weight bearing through the healthier lateral side of the joint, leading to relief of pain and discomfort. The osteotomy, once completed, is generally held by a staple implant through one or more cortices.

It is important that osteotomy cuts be performed accurately and that the completed osteotomy be stabilized in order to promote rapid healing and avoid prolonged postoperative immobilization in a cast. Prolonged immobilization in a cast can lead to persistent stiffness and prolonged rehabilitation. Accurate cuts also relieve pain and provide better clinical results, such as a better gait and avoidance of total knee arthroplasty.

Kirkley (U.S. Pat. No. 4,335,715, Jun. 22, 1982) relates to an apparatus wherein a pair of pins positioned on an arcuate track are inserted into the bone to serve as a guide for the surgeon in making cuts. Chambers (U.S. Pat. No. 4,349,018, Sep. 14, 1982) discloses an assemblage for guiding saw cuts to be made during a proximal tibia osteotomy or a total knee replacement operation. Slocum (U.S. Pat. No. 4,565,191, Jan. 21, 1986) relates to an apparatus for performing cuneiform osteotomy which includes a jig and an osteotomy guide. Reese (U.S. Pat. No. 4,750,481, Jun. 14, 1988) relates to a set of appliances which include a follower adapted to be positioned within a first saw cut and a saw guide movably positionable with respect to the follower and adapted to be set and held in a position to guide the saw for a second cut. Comparetto (U.S. Pat. No. 4,952,214, Aug. 28, 1990) relates to a saw guide with two intersecting slots, wherein the main slot is arcuate and is used to make a curved cut in a bone, and the other slot is either straight or arcuate and is used to cut a wedge-shaped section from the bone. Hofmann et al. (U.S. Pat. No. 5,021,056, Jun. 4, 1991) relates to an apparatus for performing osteotomy which includes a transverse alignment guide, an osteotomy guide, and a fixation plate. Schreiber (U.S. Pat. No. 5,246,444, Sep. 21, 1993) relates to an osteotomy device and method that allows a surgeon to establish a reference external to the bone as to the position of the apex and angle of the wedge to be cut and then to make use of an integral saw guide to translate those references into the bone as saw cuts. All references cited herein, including the foregoing, are incorporated herein in their entireties.

It is an object of the present invention to provide instrumentation which allows a surgeon to make accurate transverse and angular cuts. In particular, it is an object to provide instrumentation which allows a surgeon to produce smooth osteotomy surfaces which come together in a flush manner when the osteotomy is closed. It is yet a further object of the present invention to provide a method of performing osteotomy.

SUMMARY OF THE INVENTION

Broadly, the present invention relates to an apparatus for stabilizing a saw blade during the performance of a cut in a bone. The apparatus has (a) a stabilizer with a body having at least one outwardly projecting element wherein said element is capable of being inserted into an existing cut in the bone; (b) a cutting guide with a body having at least one slot therein for guiding a saw blade to the bone at a predetermined angle; and (c) attachment means for removably attaching said stabilizer to said cutting guide, said attachment means being movably adjustable along an axis which is essentially parallel to the longitudinal axis of the bone. The apparatus can further have indicia to assist a user in choosing a position to removably attach said stabilizer to said cutting guide. When said existing cut is a transverse cut having a known depth, said apparatus can further have a reference point that can be aligned with the indicia which corresponds to the depth of the transverse cut, such that a resulting angle cut will intersect with the transverse cut to produce an osteotomy having a bony hinge. The point of intersection of the existing cut and the transverse cut can be at about the point of transition between hard bone and soft bone, or in soft bone within about 5 mm from hard bone. The indicia is preferably on the cutting guide and the reference point is preferably on the stabilizer. The body of said stabilizer may have at least one hole for placement over an existing drill bit extending from the bone, or at least two holes for placement over an existing drill bit extending from the bone and over an existing stabilizing pin extending from the bone.

Another embodiment of the present invention relates to an apparatus for stabilizing a drill bit during the drilling of a hole in a bone. The apparatus has (a) a stabilizer with a body having at least one outwardly projecting element wherein said element is capable of being inserted into an existing cut in the bone; (b) a hole guide with a body having at least one hole for guiding a drill bit to the bone at a predetermined angle; and (c) attachment means for removably attaching said stabilizer to said hole guide, said attachment means being movably adjustable along an axis which is essentially parallel to the longitudinal axis of the bone. The attachment means may further comprise indicia to assist a user in choosing a position to removably attach said stabilizer to said hole guide. The body of said stabilizer may have at least one hole for placement over an existing drill bit extending from the bone; or at least two holes for placement over an existing drill bit extending from the bone and over an existing stabilizing pin extending from the bone.

Another embodiment of the present invention relates to an apparatus for stabilizing a saw blade during the performance of a cut in a bone and stabilizing a drill bit during the drilling of a hole in the bone. The apparatus has (a) a stabilizer with a body having at least one outwardly projecting element, wherein said element is capable of being inserted into an existing cut in the bone; (b) a cutting guide with a body having at least one slot for guiding a saw blade to the bone at a predetermined angle; (c) a hole guide with a body having at least one hole for guiding a drill bit to the bone at a predetermined angle; and (d) attachment means for sequentially removably attaching said stabilizer to said cutting guide and said stabilizer to said hole guide, said attachment means being movably adjustable along an axis which is essentially parallel to the longitudinal axis of the bone. The apparatus may further comprise indicia to assist a user in choosing a position to removably attach said stabilizer to said cutting guide. When the existing cut is a transverse cut having a known depth, said apparatus may further have a reference point that can be aligned with the indicia which corresponds to the depth of the transverse cut, such that a resulting angle cut will intersect with the transverse cut to produce an osteotomy having a bony hinge. The point of intersection of the existing cut and the transverse cut will preferably be in soft bone within about 5 mm from hard bone.

Another embodiment of the present invention relates to an apparatus for performing an angled cut in a bone. The apparatus has (a) a drill bit for placement in the bone such that at least part of the drill bit extends from the bone; (b) a stabilizing pin for placement in the bone such that at least part of the stabilizing pin extends from the bone; (c) a stabilizer with a body having at least one outwardly projecting element capable of being inserted into an existing cut in the bone, the body also having at least two holes for placement over said drill bit and said stabilizing pin; (d) a cutting guide comprising a body and having at least one slot for guiding a saw blade to the bone at a predetermined angle; (e) attachment means for removably attaching said stabilizer to said cutting guide, said attachment means being movably adjustable along an axis which is essentially parallel to the longitudinal axis of the bone; and (f) a saw blade for insertion into a slot in said cutting guide for cutting the bone. The apparatus may further comprise indicia to assist a user in choosing a position to removably attach said stabilizer to said cutting guide. When the existing cut is a transverse cut having a known depth, said apparatus further comprising a reference point that can be aligned with the indicia which corresponds to the depth of the transverse cut, such that a resulting angle cut will intersect with the transverse cut to produce an osteotomy having a bony hinge. The point of intersection of the existing cut and the transverse cut will preferably be in soft bone within about 5 mm from hard bone.

Another embodiment of the present invention relates to an apparatus for drilling a hole in a bone. The apparatus has a first drill bit for placement in the bone such that at least part of the drill bit extends from the bone; (b) a stabilizing pin for placement in the bone such that at least part of the stabilizing pin extends from the bone; (c) a stabilizer with a body having at least one projecting element capable of being inserted into an existing cut in the bone and having at least two holes for placement over said drill bit and said stabilizing pin; (d) a hole guide with a body having at least one hole for guiding a second drill bit to the bone at a predetermined angle; (e) attachment means for removably attaching said stabilizer to said hole guide, said attachment means being movably adjustable along an axis which is essentially parallel to the longitudinal axis of the bone; and (f) a second drill bit for insertion into a hole in said hole guide means for drilling a hole in the bone. The attachment means may further comprise indicia to assist a user in choosing a position to removably attach said stabilizer to said hole guide.

Another embodiment of the present invention relates to a method of performing an osteotomy having the steps of (a) performing a transverse cut in a bone; (b) measuring the depth of said transverse cut; (c) positioning a stabilizing means in relation to a cutting guide means such that a reference point on either of said stabilizing means or cutting guide means is aligned with an indicia value on said other means which corresponds with the depth of the transverse cut, and wherein said stabilizing means has at least one projecting element for insertion into the transverse cut and said cutting guide means has at least one slot for guiding a saw blade to the bone at a predetermined angle; (d) inserting said at least one projecting element of said stabilizing means into the transverse cut; and (e) inserting a saw blade into a slot in said cutting guide means and cutting the bone at a predetermined angle for a predetermined length to intersect the transverse cut and thereby produce a wedge of bone.

Another embodiment of the present invention relates to a method of performing an osteotomy having the steps of (a) performing a transverse cut in a bone; (b) attaching a stabilizing means to a cutting guide means, wherein said stabilizing means has at least one projecting element for insertion into the transverse cut and the cutting guide means has at least one slot for guiding a saw blade to the bone at a predetermined angle; (c) inserting said at least one projecting element of said stabilizing means into the transverse cut; (d) inserting a saw blade into a slot in said cutting guide means and cutting the bone at a predetermined angle for a predetermined length to intersect the transverse cut and thereby produce a wedge of bone; (e) removing said saw blade, said stabilizing means, said cutting guide means, and said wedge of bone; (f) closing the resulting bone faces; (g) attaching a stabilizing means to a distal hole guide means, wherein said stabilizing means has at least one projecting element for insertion into the transverse cut and the distal hole guide means has at least one hole for guiding a drill bit to the bone at a predetermined angle; (h) inserting said at least one projecting element of said stabilizing means into the transverse cut; (i) inserting a drill bit into a hole in said distal hole guide means and drilling a distal hole; (j) removing said drill bit; and (k) inserting an implant to hold said bone faces against each other.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIGS. 16–18 show variations of intersections between a transverse and angle cuts.

DETAILED DESCRIPTION OF THE INVENTION

Prior to the osteotomy, an arthroscope may be inserted into the knee joint to debride out meniscus tears, perform a synovectomy, and wash out the joint. Before removing the arthroscope, a K-wire may be inserted across the knee under arthroscopic visualization to determine the location of the joint line. Once the K-wire is in place, the arthroscope and its instruments are removed.

A surgeon will choose which type of incision to make based on his or her experiences and patient considerations. Common incisions are straight, oblique incisions from the tibial tubercle to the fibular head, and L-shaped incisions made along the lateral joint line proceeding anteriorly to the anterior border of the tibia to the level of the tibial tubercle.

After the incision is made, the soft tissues may be incised and an electrocautery knife may be run around the origin of the anterior tibial muscles. This may be followed by periosteal stripping in both directions.

A shortening procedure performed on the fibula will facilitate closure of the tibial osteotomy. Fibular shortening can be achieved by any of the following: (a) disarticulation of the proximal tibiofibular joint; (b) oblique osteotomy through the head of the fibula; (c) resection of a portion of the fibula at the level of the tibial osteotomy; and/or (d) oblique osteotomy of the fibula at its mid-shaft.

Once the fibular osteotomy has been completed, a retractor may be placed behind the tibia to protect vital soft tissues from the osteotomy saw. Similar retraction may be applied under the patellar tendon anteriorly.

Figure 1:
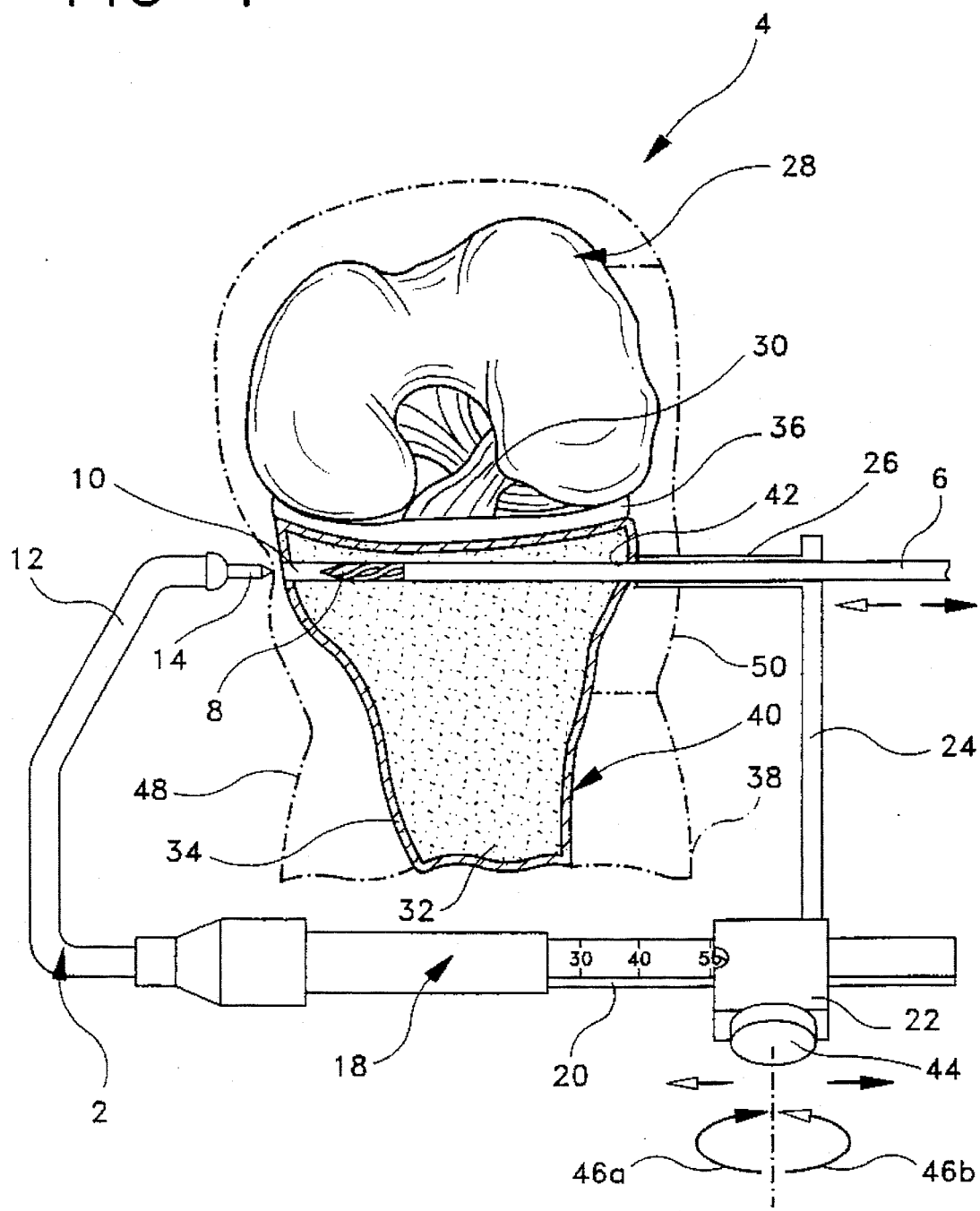
FIG. 1 is an isometric view of a transverse drill guide of the present invention.

With reference to FIG. 1, before making a transverse cut, a transverse drill guide 2 is attached to the medial and lateral aspects of the proximal tibia. The transverse drill guide 2 is shown across the proximal tibia 40 and the knee 4. The transverse drill guide 2 has a guide pin arm 12 which holds a guide pin 14 against the flesh and/or bone. The handle 18 can be grasped by the surgeon to position the transverse drill guide 2. Guide bar 20 may contain calibrated markings to indicate the depth of the drill hole. A locking block 22 may lock the transverse drill guide into place when set screw 44 is tightened. Direction 46(b) loosens set screw 44, and direction 46(a) tightens set screw 44. The drill guide support arm 24 may be in unitary construction with a collar 26. Preferably, collar 26 will define a hole having a first diameter, and a second collar can be inserted into said first hole having a second diameter. The collar can be removed to uncover a hole having a second diameter, so that different sized drill bits and/or pins can be inserted via many types of fasteners known to those skilled the art through the transverse drill guide. In this embodiment, the collar 26 has a toothed end 42. Shown in the knee are ligaments 30, soft bone 32, hard bone 34, cartilage 36, flesh 38, and the femoral condyles 28.

The transverse drill guide 2 places a drill bit 6 across the proximal tibia 40. The drill bit 6 will preferably be about 5.0 mm in diameter, and will have a drill head 8. The drill prepares a hole 10 for the proximal section of the implant and provides stability, with a guide pin, for the cutting instruments. The drill bit will preferably be as close to the maximum A/P diameter of the proximal tibia as possible. Too much posterior placement of the drill (such as less than 25 mm from the fibular head) could result in the cutting instrument being blocked by the fibular head, if still attached.

The set screw 44 is loosened to adjust the width. The medial side 48 penetrates the skin and may contact bone while the lateral side 50 rests on the exposed bone. The guide is aligned so that it is preferably, at center, about 5 mm to about 10 mm below the joint line. The transverse cut will be about 10 mm below the line defined by drill bit 6 and stabilizing pin 68. Further distal location of the transverse cut is generally not desirable because an adequate lateral shelf would not be provided after wedge removal for support of the proximal tibia. Also, the angle cut could be made too close to, or through, the tibial tubercle.

After the width is suitably adjusted, set screw 44 is tightened. The body of transverse drill guide 2 may be radiolucent so that fluoroscopy can be used to align the transverse axis of the drill guide with the transverse axis of the joint. Preferably, handle 18 and guide bar 20 will be radiolucent. Fluoroscopy can also be used to ensure that drill bit 6 and stabilizing pin 68 are inserted on the same plane and at the same angle.

Drill bit 6 is placed through the drill guide 2 and passed across the proximal tibia 40 until it just exits cortical bone on the medial side 48. With the drill bit 6 still in place, the drill guide 2 is disassembled and removed.

Figure 2:
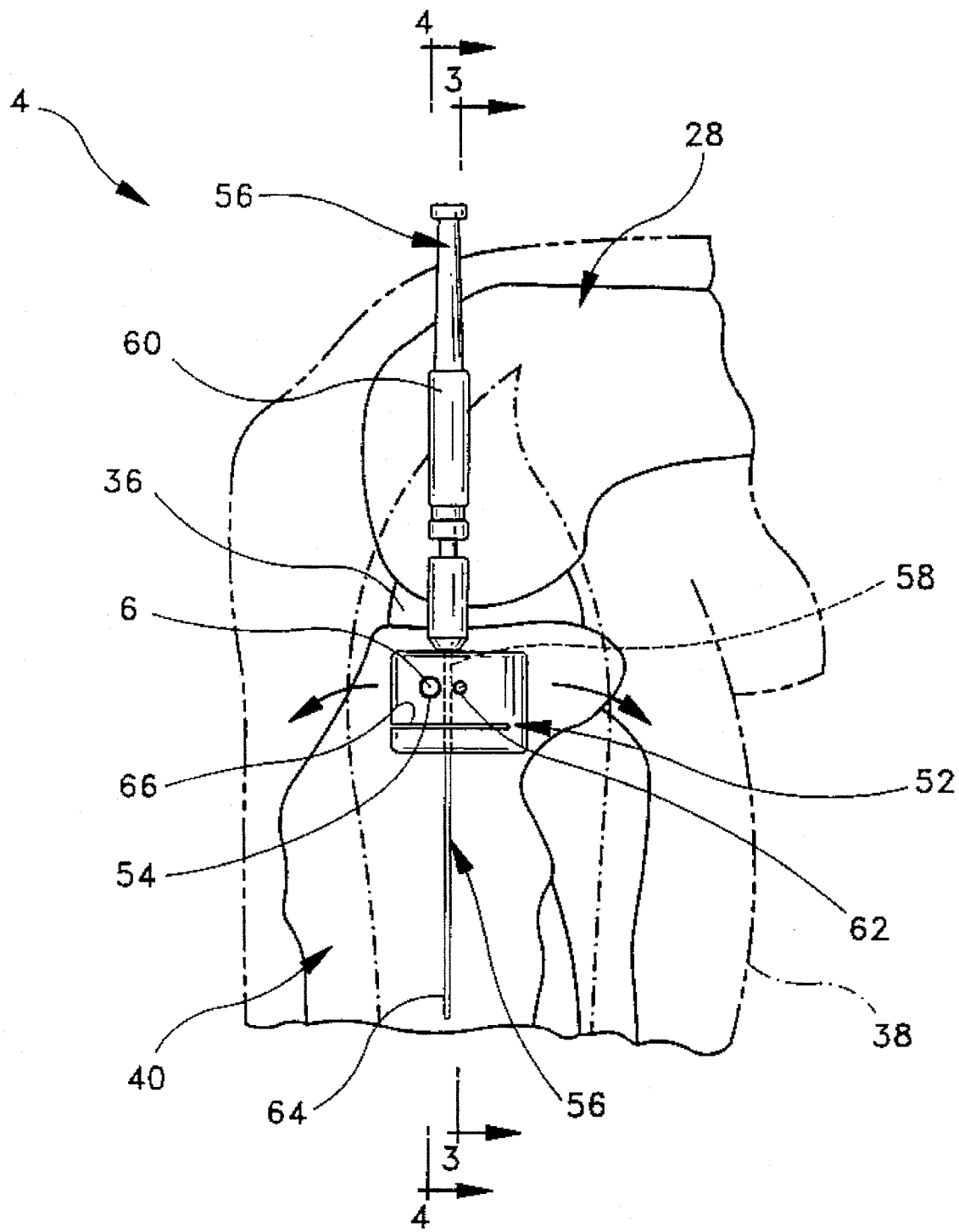
FIG. 2 is a lateral view showing a transverse cutting block and a centering pin of the present invention.
Figure 3:
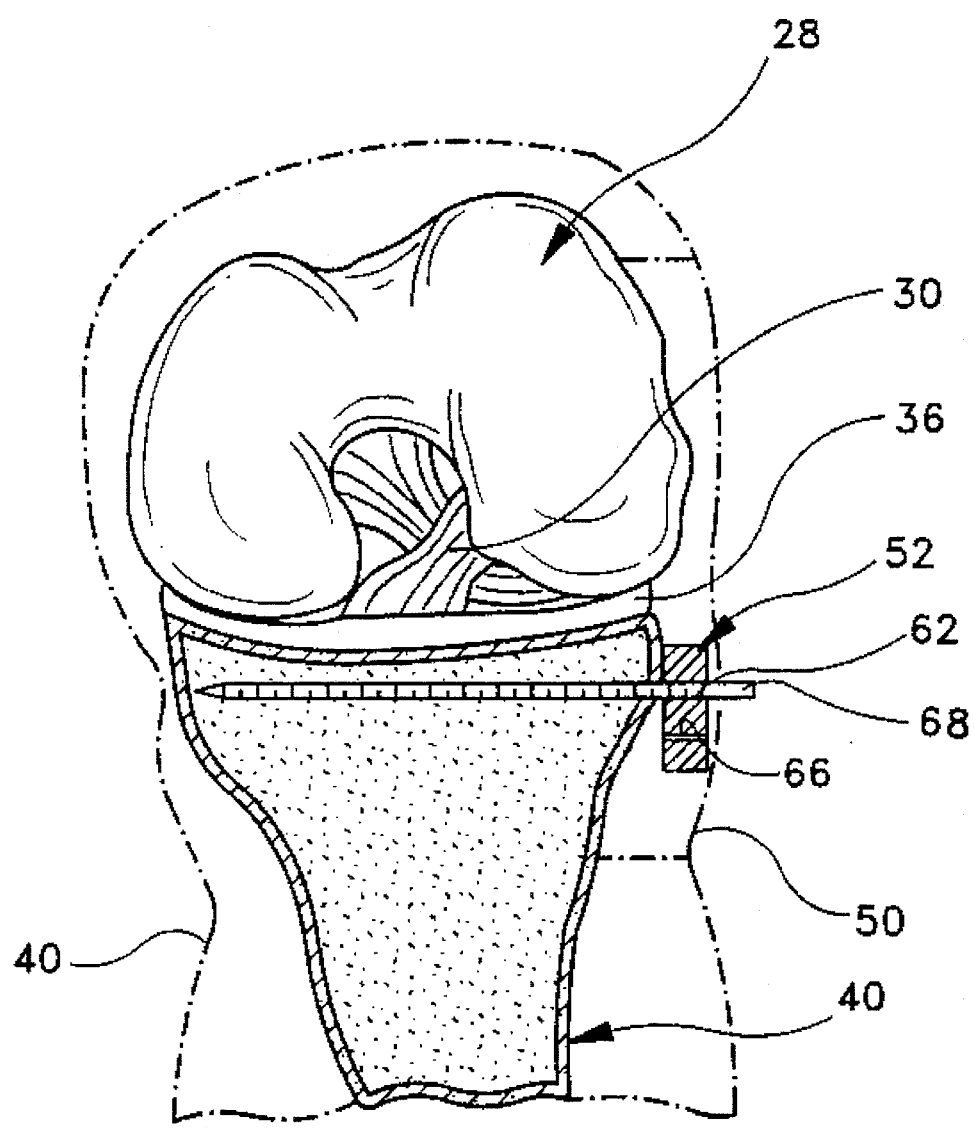
FIG. 3 is a front view showing a transverse cutting block and a stabilizing pin of the present invention.

With reference to FIGS. 2 and 3, the left or right side of the transverse cutting block 52 is slid over the drill bit 6 through a first hole 54. Centering pin 56 is placed into the centering pin hole 58. The centering pin 56 will preferably be about 2.0 mm in diameter and will have a handle 60 and a distal end 64. From the superior aspect of the transverse cutting block 52, the centering pin 56 is dropped through the centering pin hole 58. The transverse cutting block 52 is generally aligned so that the centering pin 56 is in line with the long axis of the tibia. An advantage of the centering pin 56 is that it is simple to determine its position, and therefore the position of the transverse cutting block 52, in relation to the longitudinal axis of the leg. In other words, it is easy to "line-up" the centering pin 56 with the longitudinal axis of the leg. Optionally, a surgeon may tilt the transverse cutting block 52 somewhat with the centering pin 56 to provide for flexion or extension. Once positioned, a stabilizing pin 68 is placed through a corresponding stabilizing pin hole 62 in the transverse cutting block 52 and across the tibia. The stabilizing pin 68 can be inserted in the same manner as the drill bit 6, or it can be inserted by a different manner such as by tapping. Both the stabilizing pin 68 and the drill 6 remain in the bone to stabilize the transverse cutting block 52. The stabilizing pin 68 is preferably calibrated to indicate the depth of the inserted stabilizing pin 68. The centering pin 56 is then removed.

After the stabilizing pin 68 is positioned, fluoroscopy can be utilized to determine the suitability of the stabilizing pin 68 and drill bit 6 depths and angles. If necessary, corrective measures can be taken to adjust such depths or angles.

Figure 4:
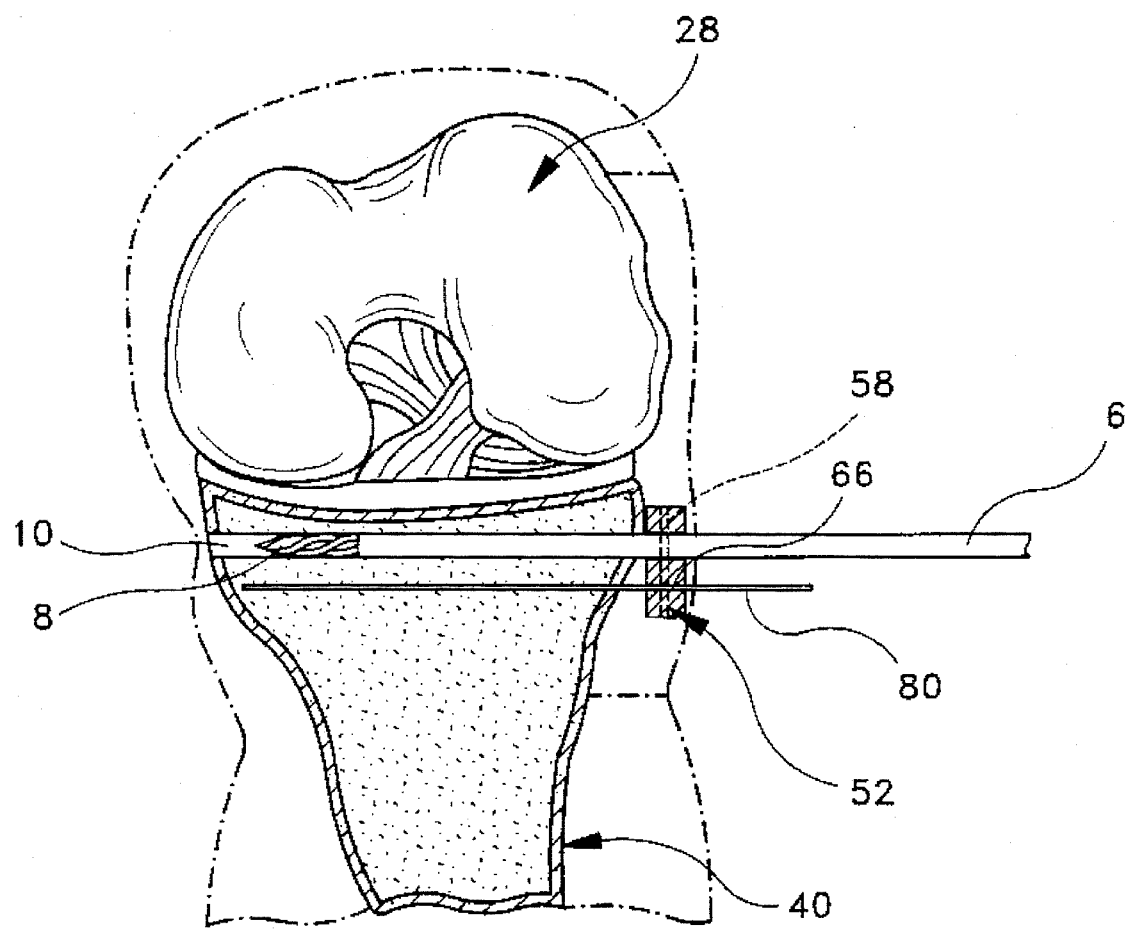
FIG. 4 is a front view showing the transverse cutting block and the stabilizing pin of FIG. 3, with a transverse saw blade in the knee.
Figure 5:
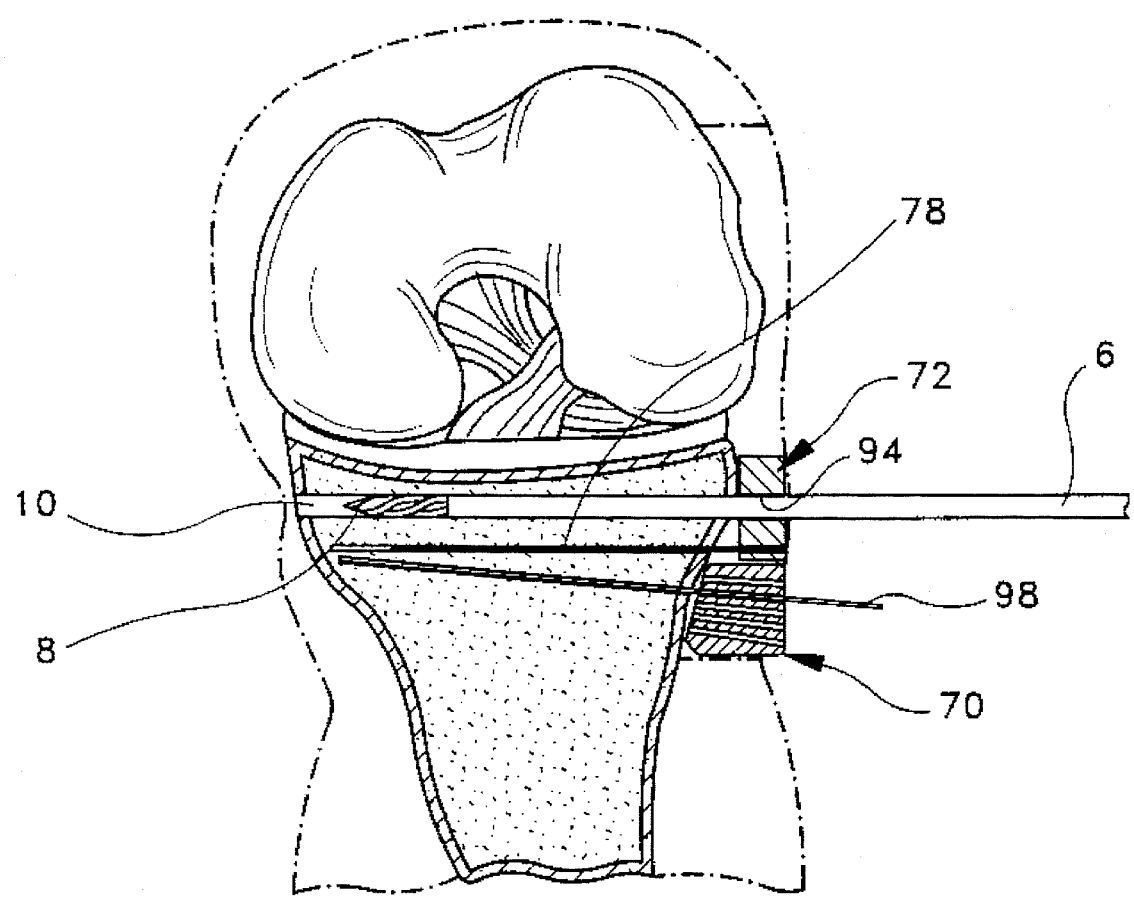
FIG. 5 is a front view of a stabilizing block and an angle cutting block of the present invention with an angle saw blade in the tibia.
Figure 6:
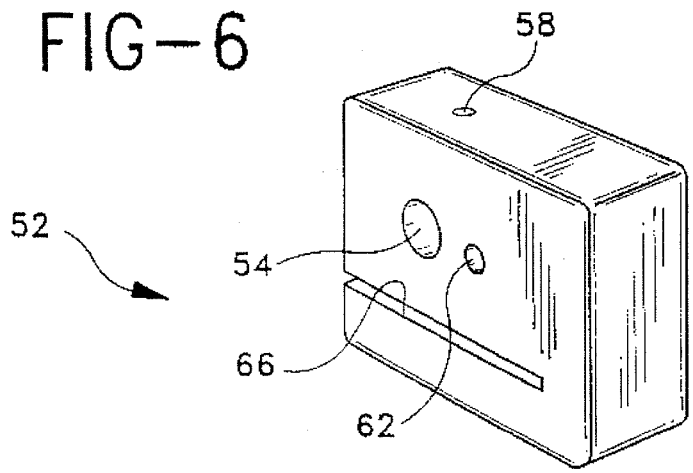
FIG. 6 is an isometric view of a transverse cutting block of the present invention.

With reference to FIGS. 4 and 6, the transverse cutting block 52 will preferably rest flush against the bone to provide accuracy and to facilitate measurement of the depth of the transverse cut and stabilizing pin 68. The transverse cut will be about 10 mm below the center of the stabilizing pin 68 and the drill bit 6, a total distance from the joint line of about 15 mm to about 20 mm. An appropriate transverse saw blade 80 is attached to a power unit (not shown). The transverse saw blade 80 will preferably be calibrated so that the depth of the cut is known. The blade is inserted into the slot 66 in the transverse cutting block 52. The slot 66 will guide the transverse saw blade 80 to provide a precise transverse cut and avoid any anterior/posterior or varus/valgus tilt. The transverse cut should go across the tibia up to the medial side 48, leaving a preoperatively determined amount of bone intact.

The distance cut can be measured by reading the length off the transverse saw blade 80 while the transverse cutting block 52 is still in place. The calibrations on the transverse saw blade 80 compensate for the depth of the transverse cutting block 52. Transverse saw blade 80 and transverse cutting block 52 are then removed. Drill bit 6 and stabilizing pin 68 are left in position.

Figure 7:
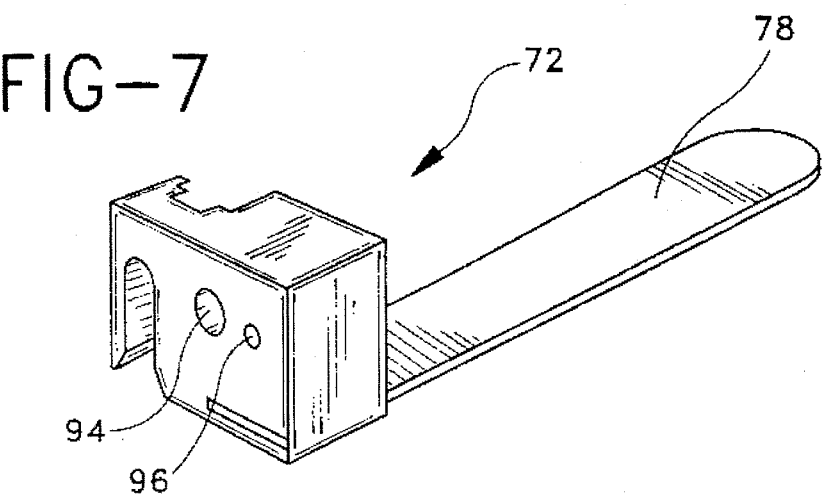
FIG. 7 is an isometric view of a stabilizing base of the present invention.
Figure 8:
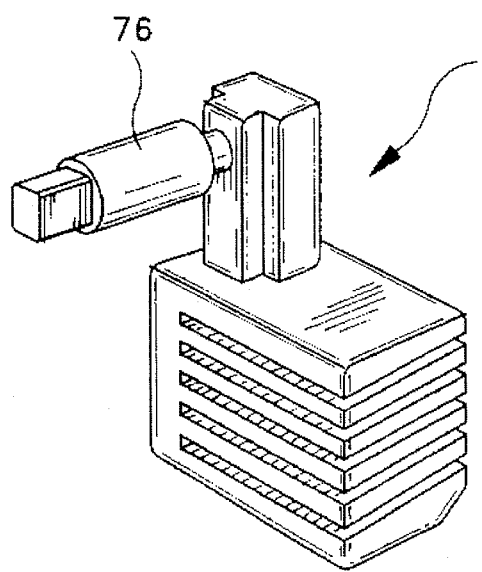
FIG. 8 is an isometric view of an angle cutting block of the present invention.
Figure 9:
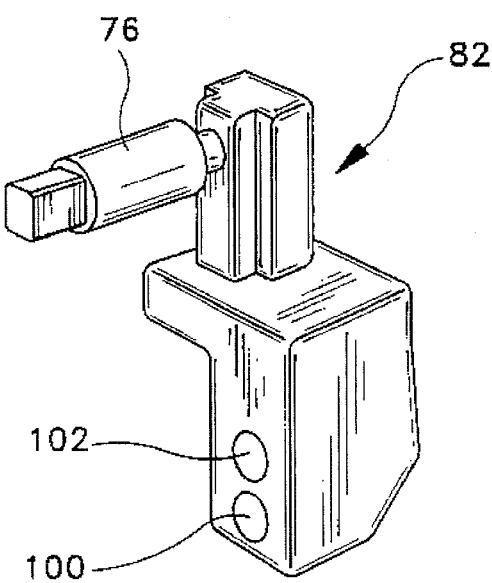
FIG. 9 is an isometric view of a secondary drill block of the present invention.
Figure 10:
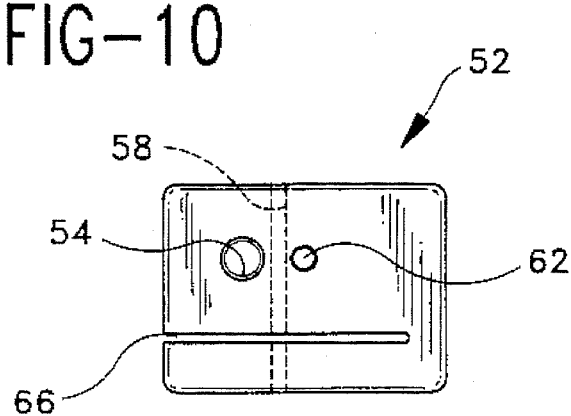
FIG. 10 is a front view showing the transverse cutting block of the present invention.
Figure 11:
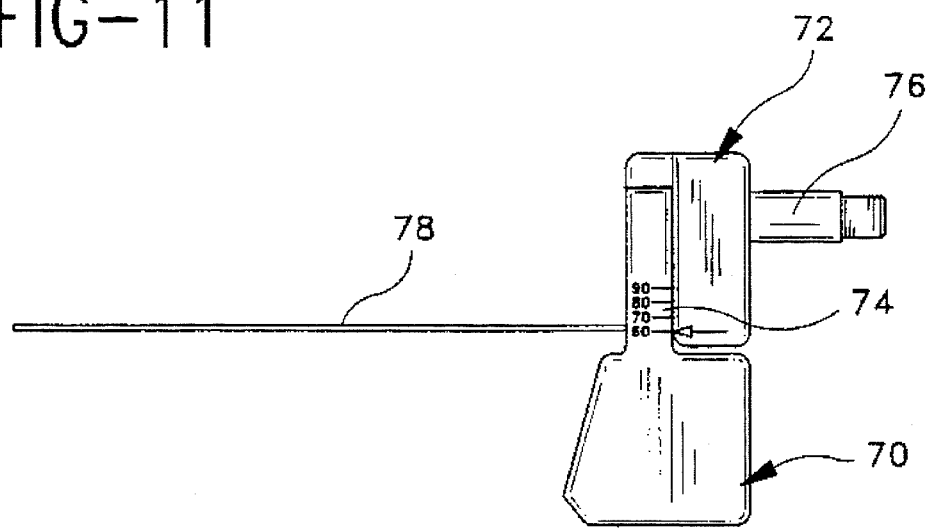
FIG. 11 is a side view showing a stabilizing base of the present invention removably attached to an angle cutting block.
Figure 12:
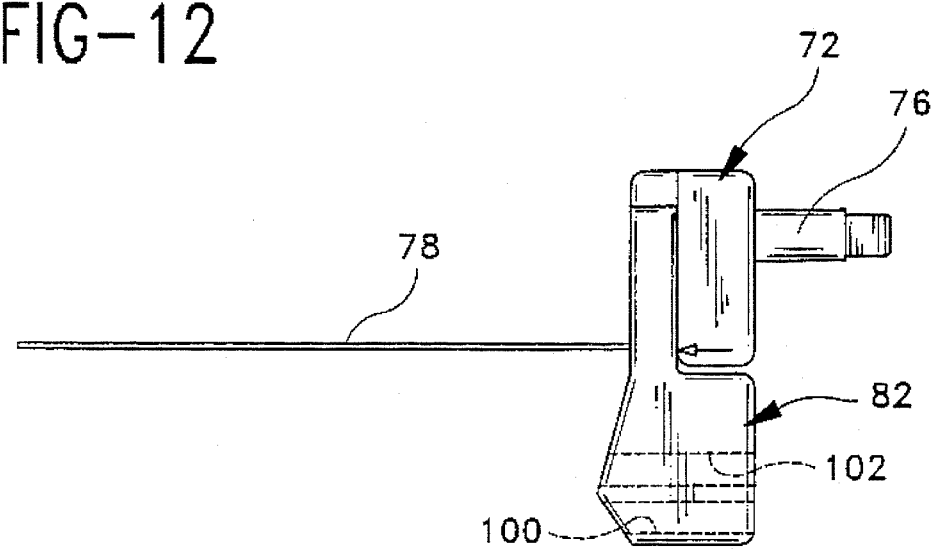
FIG. 12 is a side view showing a stabilizing base of the present invention removably attached to a secondary drill block of the present invention.

With reference to FIGS. 5 and 7–12, the angle cut is made by removably attaching the left or right angle cutting block 70 to the appropriate stabilizing base 72. FIG. 7 shows one embodiment of stabilizing base 72 of the present invention. In other variations, rather than a single tongue 78, there will be more than one element extending from the base. There may be more than two holes. FIG. 8 shows one embodiment of the cutting guide means of the present invention. In other embodiments, there will only be a single slot. Other variations may exist. On the set screw 76 side of the angle cutting block 70 are preferably calibrations 74 corresponding to the depth of the transverse cut. The set screw 76 is loosened and the transverse cut depth is lined-up with the arrow. The transverse cut depth can be determined by, e.g., a calibrated saw blade 80, the transverse drill guide 2, and/or a calibrated stabilizing pin 68. The set screw 76 may be tightened with a T-wrench to ensure that the correct angle is maintained during cutting. The set screws 76 shown in FIG. 11 and 12 represent just one embodiment of the attachment means of the present invention. The attachment means for removably attaching the stabilizing base to the cutting guide is movably adjustable along an axis which is essentially parallel to the longitudinal axis of the bone. Other possible adjustable means include, but are not limited to, a dovetail, a track, or a threaded member. The assembly is placed over the drill bit 6 through a first stabilizing base hole 94 and over the stabilizing pin 68 through a second stabilizing base hole 96. The tongue 78 of the stabilizing base 72 is inserted into the transverse cut. The cutting block/stabilizing base assembly is now stabilized for the angle cut. With the assembly flush against the bone, the angle cut will intercept the end of the transverse cut, resulting in a complete wedge osteotomy. The angle saw blade 98 is placed in the desired angle and the wedge is cut. The angle saw blade 98 may be the same as the transverse saw blade 80. Preferably, a bony hinge 116 will remain after the wedge is removed. In general, it is desirable that the point of intersection between the transverse and angle cuts is at about the transition point between hard and soft bone, and optionally in the soft bone between the transition point and within about 5 mm of the hard bone.

Figure 13:
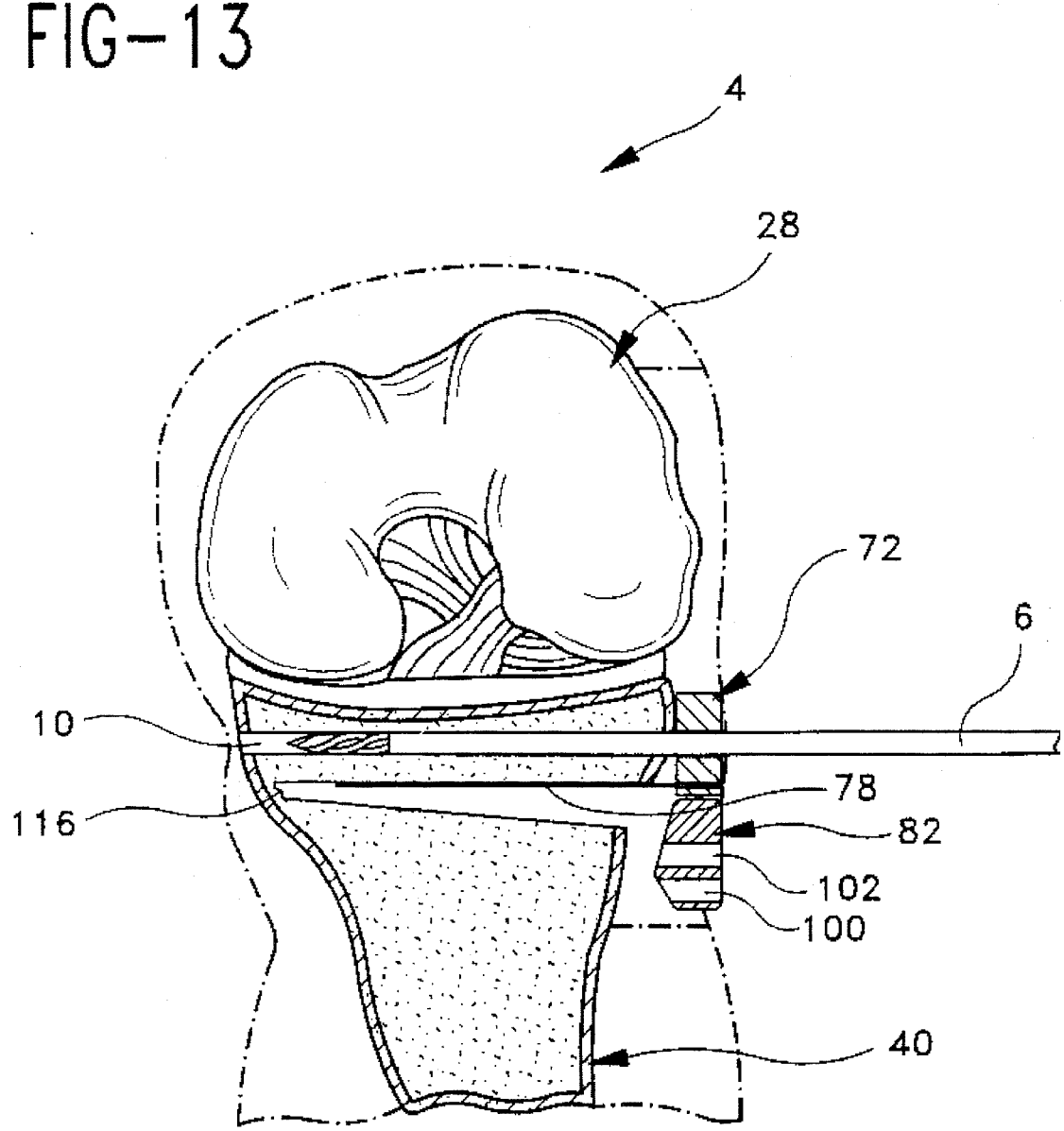
FIG. 13 is a front view showing the stabilizing base of FIG. 12 removably attached to the secondary drill guide of FIG. 12.

The angle saw blade 98, the angle cutting block 70, and the stabilizing base 72 are removed. The wedge is removed and the osteotomy is completed as needed. As shown in FIG. 13, both the transverse and angle saw cuts are planar so that the severed bone faces can mate uniformly to promote rapid and structurally effective mending of the bone.

Figure 14:
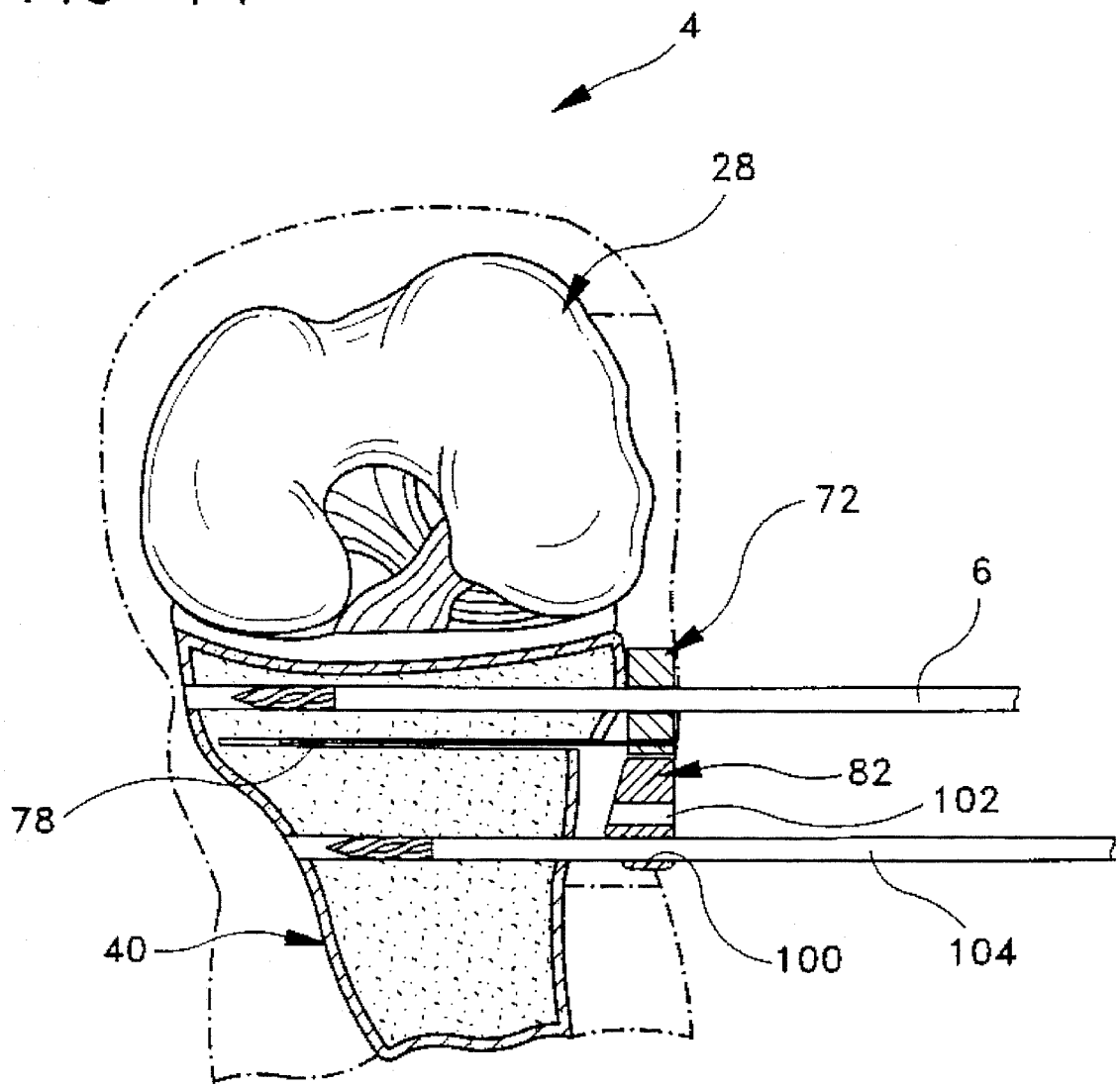
FIG. 14 is a front view of the stabilizing base and secondary drill block of FIG. 13 showing the secondary drill bit inserted in the knee.

With reference to FIGS. 13 and 14, the distal hole drill block 82 is removably attached to the stabilizing base 72 and placed over the stabilizing pin 68 and the drill bit 6. In most cases, the distal hole 100 in the drill guide will be used to drill the hole for the distal implant segment. The distal hole drill block 82 is generally pushed completely into the stabilizing base 72 and secured by tightening the set screw 76 with a T-wrench. Optionally, the distal hole drill block 82 can be movably adjustable in relation to the stabilizing base 72.

To avoid divergent drill holes, the osteotomy should be completely closed. The osteotomy may be closed with valgus manipulation. A distal hole is drilled across the diaphysis of the tibia with a distal drill bit 104, exiting the far cortex. The hole will preferably be about 5.0 min. The distal hole drill block 82, the stabilizing base 72, the proximal drill 6, and the stabilizing pin 68 are removed.

Figure 15:
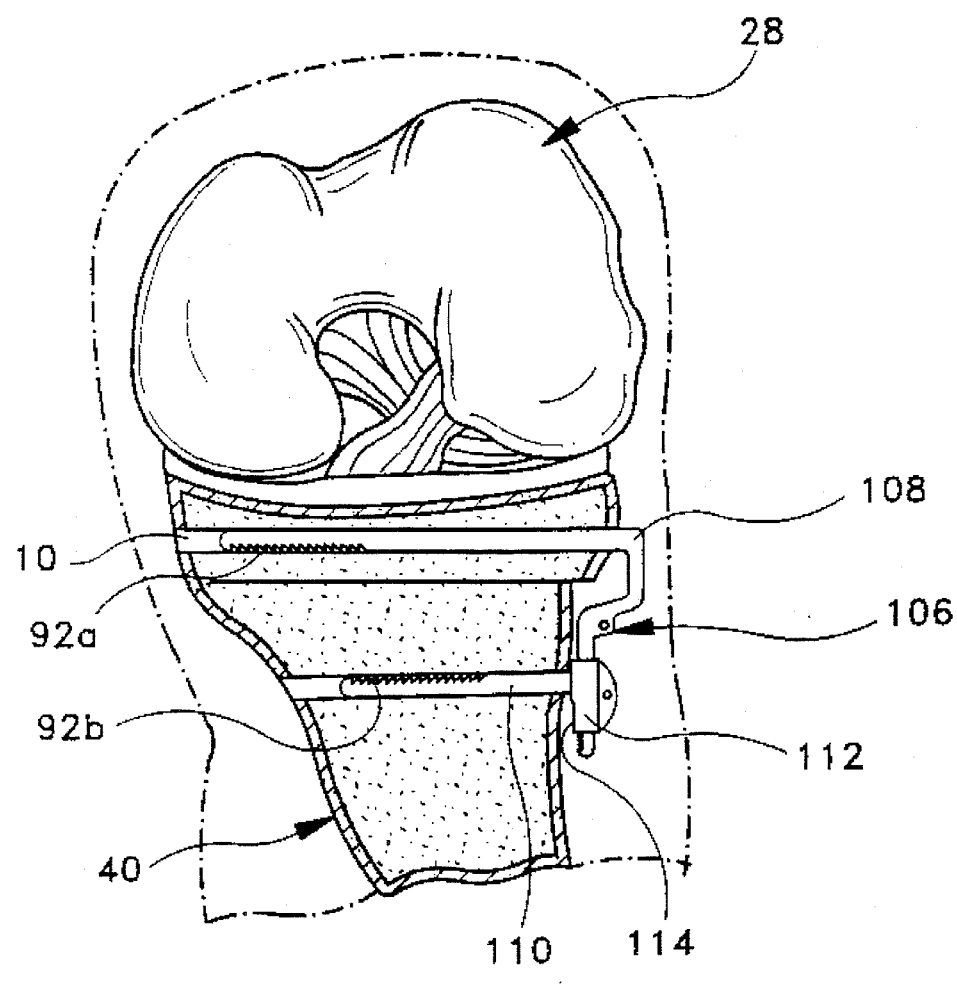
FIG. 15 is a side view of an implant inserted in a knee following osteotomy.

With reference to FIG. 15, the implant 106, which will be referenced directly from the transverse and angle cutting instrumentation, provides compression while providing strength for early patient mobility. The implant 108 is an assembly of a proximal component 108 and a distal component 110. Proximal components 108 can be made in variable configurations, such as 5 mm, 10 mm, or 15 mm, thus allowing for conformity over the tibial plateau. A ratchet column 112 provides one-way travel of the distal component towards the proximal component to create compression. Each distal component contains a leaf spring 114, which engages the ratchet section of the proximal component 108. Both proximal components 108 and distal components 110 is preferably made of Vitallium® Alloy metal to provide higher strength over other metals and to ensure a stable wedge osteotomy closure. An example of an appropriate implant is found in U.S. Pat. No. 4,852,558.

The implant 106 may be inserted as follows: By using a depth gauge which has been calibrated for this system, proximal and distal depth measurements are taken through the proximal and distal drill holes. For the distal measurement, preferably add about 5 mm to the depth indicated. The distal component will generally not rest flush against the tibial diaphysis due to the contour of the metaphyseal/diaphyseal region.

Proximal implant components 108 and distal implant components 110 are selected which best fit the depth readings for bicortical purchase. The proximal component 108 is first inserted onto the distal component 110. The leaf spring 114 of the distal component should always face away from the proximal component.

With the compression pliers in place, the implant is positioned until the legs 92(*a,b*) of the implant are aligned with the drill holes in the closed osteotomy. If the distal component 110 of the implant travels too far along the proximal component, the implant distractor will allow the distal component's 110 spring to be disengaged and the two components will separate. The implant 106 can then be reassembled to the desired position.

The implant 106 is press fit into the drill holes until the lateral aspect of the implant is flush against the bone. The implant 106 may be tapped lightly, if necessary. The implant 106 should then be closed until the osteotomy is completely closed. The knee should be checked for a full range of motion prior to closing.

At closing, the ilio-tibial band ("I-T band") may be imbricated and a drain is inserted subcutaneously and against bone. Both limbs of the drain are used to help avoid compartment syndrome. After closing, the knee is wrapped with a dry, sterile dressing over the drain that has been left in the incision. The patient should be placed on a continuous passive motion ("CPM machine") in a recovery room. On the following day, the patient may begin physical therapy, advancing from weight bearing as tolerated to full weight bearing within approximately two weeks. The CPM machine should allow range of motion up to 90 degrees. The patient should become active with a range of motion between 0 to 90 degrees. The patient may perform straight leg raises and do short arc quadriceps exercises in order to regain quadriceps tone.

At the end of two weeks, the patient should be able to have excellent control of the thigh with straight leg raising and short arc quad exercises. The patient should have 90 degrees of range of motion and should be fully weight bearing with crutches. The patient will then advance to a cane, and then to full weight bearing without side support and without a brace at the end of four weeks.

The implant 106 can be removed at about the sixth postoperative month, if desired. To facilitate removal, the implant retractor is attached to release the compression on the implant. Then, the extractor is attached to a McReynolds driver. The hook is placed under the implant and driven out.

In disassembling the insert 106, the distal segment 110 of the implant 106 can not be removed in a conventional manner from the proximal component 108 as the ratchet allows only one direction of travel. To disassemble the implant 106, an implant distractor instrument is needed. Take the instrument and check that the tines are completely closed. If not, lift up the rear crossbar, and the tines will then spring together. Then check that the spring distraction screw is drawn into its maximum, which is achieved by turning the knob counterclockwise until the fork is drawn away from the tip of the tines. The handle is then squeezed to open the tines, aligning them with the instrument holes in the implant and the distraction fork in line with the distal component spring. The tip of each tine is then placed into the holes.

The knob of the distraction spring is then turned clockwise to allow the fork to engage the spring. When resistance is felt, the knob is turned more until the fork pushes the spring away from the proximal component's 108 ratchet section. The knob turning is then stopped. The handle is squeezed and the two components 108, 110 are completely separated from each other. The implant 106 may now be reassembled for implantation. The distraction instrument can also be used at the time of implant removal to release tension for easier removal.

A high tibial osteotomy performed according to the foregoing procedure is an effective means of treating unicompartmental degenerative arthritis of the knee. This technique can align the lower extremity such that the axis of weight bearing is shared between the medial joint compartment and the lateral joint compartment. Thus, in cases where arthritis predominantly affects the medial joint compartment, this procedure directs the forces of weight bearing through the healthier lateral side of the joint, leading to relief of pain and discomfort. The osteotomy cuts can be performed accurately and the completed osteotomy can be stabilized in order to promote rapid healing and avoid prolonged postoperative immobilization in a cast which can lead to persistent stiffness and prolonged rehabilitation.

In general, a preferable high tibial osteotomy is made by producing two cuts in the bone that are at acute angles to each other in the anterior-posterior plane of the tibia. The acute angle may be selected by: pre-operative x-rays, amount of pain, amount of degenerative disease, and/or the activity of the patient (e.g., young laborer vs. old office worker). The angle cutting guide can be introduced into the surgery after the transverse cut has been made and its depth in the bone is known. Since the required angle is known and the end point of the transverse cut line is known, the angle cut guide position can be adjusted to give the proper vertical position of the angle cut. FIGS. 16–18 show variations of angle cuts with a proper vertical position, a vertical position that is too long, and a vertical position that is too short.

According to geometric principles, any right triangle can be defined by a height and an angle. The base of the triangle can be calculated mathematically. The angle is determined pre-operatively, and the height is the depth of the first cut.

The calibration on the transverse drill guide, the stabilizing pin, and the saw blade will all give the height measurement for the right triangle. The angle is known so that the base dimension can be determined mathematically. The guide can be adjusted to the correct vertical position so that the base dimension is correct.

While several examples of the present invention have been described, it is obvious that many changes and modifications may be made thereunto, without departing from the spirit and scope of the invention.

I claim:

1. A kit for stabilizing a saw blade during the performance of a cut in a bone, said apparatus comprising:

(a) a stabilizer comprising a body having at least one outwardly projecting flat, tongue-shaped element, wherein said element is capable of being inserted into an existing cut in the bone;

(b) a cutting guide comprising a body having at least one slot therein for guiding a saw blade to the bone at a predetermined angle; and (c) attachment means for removably and adjustably attaching said stabilizer to said cutting guide, said attachment means being movably adjustable along an axis which is essentially parallel to the longitudinal axis of the bone and said stabilizer and said cutting guide being movably adjustable with respect to each other and fixable in position with respect to each other by means of said attachment means, wherein the body of said stabilizer has at least one hole for placement over an existing drill bit extending from the bone.

2. The apparatus of claim 1 wherein the body of said stabilizer has at least one additional hole for placement over an existing stabilizing pin extending from the bone.

3. A kit for stabilizing a drill bit during the drilling of a hole in a bone, said apparatus comprising:

a) a stabilizer comprising a body having at least one outwardly projecting flat, tongue-shaped element, wherein said element is capable of being inserted into an existing cut in the bone;

(b) a hole guide comprising a body having at least one hole for guiding a drill bit to the bone at a predetermined angle; and (c) attachment means for removably and adjustably attaching said stabilizer to said hole guide, said attachment means being movably adjustable along an axis which is essentially parallel to the longitudinal axis of the bone and said stabilizer and said hole guide being movably adjustable with respect to each other and fixable in position with respect to each other by means of said attachment means, wherein the body of said stabilizer has at least one hole for placement over an existing drill bit extending from the bone.

4. The apparatus of claim 3 wherein the body of said stabilizer has at least one additional hole for placement over an existing stabilizing pin extending from the bone.

5. A kit for performing an angled cut in a bone, said apparatus comprising:

(a) a drill bit for placement in the bone such that at least part of the drill bit extends from the bone;

(b) a stabilizing pin for placement in the bone such that at least part of the stabilizing pin extends from the bone;

(c) a stabilizer comprising a body having at least one outwardly flat tongue-shaped projecting element capable of being inserted into an existing cut in the bone, the body also having at least two holes for placement over said drill bit and said stabilizing pin;

(d) a cutting guide comprising a body and having at least one slot for guiding a saw blade to the bone at a predetermined angle;

(e) attachment means for removably and adjustably attaching said stabilizer to said cutting guide, said attachment means being movably adjustable along an axis which is essentially parallel to the longitudinal axis of the bone and said stabilizer and said cutting guide being movably adjustable with respect to each other and fixable in position with respect to each other by means of said attachment means; and (f) a saw blade for insertion into a slot in said cutting guide for cutting the bone.

6. The apparatus of claim 5 wherein said apparatus further comprises indicia to assist a user in choosing a position to removably attach said stabilizer to said cutting guide.

7. The apparatus of claim 6 wherein said existing cut is a transverse cut having a known depth, said apparatus further comprising a reference point positioned on said stabilizer that can be aligned with the indicia which is positioned on said cutting guide, which indicia correspond to the depth of the transverse cut, such that a resulting angle cut will intersect with the transverse cut to produce an osteotomy having a bony hinge.

8. The apparatus of claim 6, wherein said existing cut is a transverse cut having a known depth, said apparatus further comprising a reference point positioned on said cutting guide that can be aligned with the indicia which positioned on said stabilizer, which indicia correspond to the depth of the transverse cut, such that a resulting angle cut will intersect with the transverse cut to produce an osteotomy having a bony hinge.

9. A kit for drilling a hole in a bone, said apparatus comprising:

(a) a first drill bit for placement in the bone such that at least part of the drill bit extends from the bone;

(b) a stabilizing pin for placement in the bone such that at least part of the stabilizing pin extends from the bone;

(c) a stabilizer comprising a body having at least one flat, tongue-shaped projecting element capable of being inserted into an existing cut in the bone and having at least two holes for placement over said drill bit and said stabilizing pin;

(d) a hole guide comprising a body having at least one hole for guiding a second drill bit to the bone at a predetermined angle;

(e) attachment means for removably and adjustably attaching said stabilizer to said hole guide, said attachment means being movably adjustable along an axis which is essentially parallel to the longitudinal axis of the bone and said stabilizer and said hole guide being movably adjustable with respect to each other and fixable in position with respect to each other by means of said attachment means; and (f) a second drill bit for insertion into a hole in said hole guide means for drilling a hole in the bone.

10. The apparatus of claim 9 wherein said attachment means further comprises indicia to assist a user in choosing a position to removably attach said stabilizer to said hole guide.

11. A method of performing an osteotomy comprising:

(a) providing an apparatus having a stabilizing means, removably attached to a cutting guide means by an attachment means, said cutting guide means having at least one slot, wherein said stabilizing means has at least one flat tongue-shaped projecting element for insertion into a transverse cut in a bone and the cutting guide means has at least one slot for guiding a saw blade to the bone at a predetermined angle;

(b) performing the transverse cut in a bone;

(c) attaching said stabilizing means to said cutting guide means;

(d) inserting said at least one flat projecting element of said stabilizing means into the transverse cut;

(e) inserting a saw blade into said at least one slot in said cutting guide means and cutting the bone at a predetermined angle measured with respect to said bone for a predetermined length measured with respect to said bone to intersect the transverse cut and thereby produce a wedge of bone and resulting bone faces;

(f) removing said saw blade, said stabilizing means, said cutting guide means, and said wedge of bone;

(g) closing said resulting bone faces;

(h) providing a hole guide means having a hole and attaching said stabilizing means to said hole guide means, (i) inserting said at least one projecting element of said stabilizing means into the transverse cut;

(j) inserting a drill bit into said hole in said second hole guide means and drilling a hole in the bone;

(k) removing said drill bit; and (l) inserting an implant into said hole in the bone to hold said bone faces against each other.

* * * * *